US010149973B2

(12) United States Patent
Raymond et al.

(10) Patent No.: US 10,149,973 B2
(45) Date of Patent: Dec. 11, 2018

(54) MULTIPART NON-UNIFORM PATIENT CONTACT INTERFACE AND METHOD OF USE

(71) Applicant: CardioThrive, Inc., Concord, CA (US)

(72) Inventors: Douglas M. Raymond, Livermore, CA (US); Peter D. Gray, Vallejo, CA (US); Walter T. Savage, Concord, CA (US); Shelley J. Savage, Concord, CA (US)

(73) Assignee: CARDIOTHRIVE, INC., Concord, CA (US)

( * ) Notice: Subject to any disclaimer, the term of this patent is extended or adjusted under 35 U.S.C. 154(b) by 182 days.

(21) Appl. No.: 14/303,546

(22) Filed: Jun. 12, 2014

(65) Prior Publication Data

US 2014/0371567 A1 Dec. 18, 2014

Related U.S. Application Data

(60) Provisional application No. 61/835,465, filed on Jun. 14, 2013, provisional application No. 61/835,478, filed on Jun. 14, 2013.

(51) Int. Cl.
*A61B 5/1455* (2006.01)
*A61N 1/04* (2006.01)
*A61B 5/0408* (2006.01)
*A61N 1/39* (2006.01)

(52) U.S. Cl.
CPC .......... *A61N 1/0476* (2013.01); *A61B 5/0408* (2013.01); *A61N 1/046* (2013.01); *A61N 1/0484* (2013.01); *A61N 1/3968* (2013.01); *A61B 5/04082* (2013.01); *A61B 5/04085* (2013.01)

(58) Field of Classification Search
None
See application file for complete search history.

(56) References Cited

U.S. PATENT DOCUMENTS

| | | | |
|---|---|---|---|
| 4,441,498 A | 4/1984 | Nordling | |
| 5,199,429 A | 4/1993 | Kroll et al. | |
| 5,240,995 A | 8/1993 | Gyory | |
| 5,290,585 A | 3/1994 | Elton | |
| 5,338,490 A | 8/1994 | Dietz | |
| 5,362,420 A | 11/1994 | Itoh | |
| 5,402,884 A | 4/1995 | Gilman et al. | |
| 5,489,624 A | 2/1996 | Kantner | |
| 5,536,768 A | 7/1996 | Kantner | |
| 5,573,668 A | 11/1996 | Grosh | |
| 5,643,252 A | 7/1997 | Waner et al. | |
| 5,658,316 A | 8/1997 | Lamond et al. | |
| 5,660,178 A | 8/1997 | Kantner | |

(Continued)

FOREIGN PATENT DOCUMENTS

| | | |
|---|---|---|
| DE | 10 2006 025864 | 12/2007 |
| EP | 1 530 983 | 5/2005 |

(Continued)

OTHER PUBLICATIONS

PCT International Search Report of PCT/US10/27346; dated Oct. 14, 2010 (4 pgs.).

(Continued)

*Primary Examiner* — Eric Winakur
*Assistant Examiner* — Marjan Fardanesh
(74) *Attorney, Agent, or Firm* — DLA Piper LLP (US)

(57) ABSTRACT

A multipart, non-uniform patient contact interface and method of use are disclosed.

16 Claims, 7 Drawing Sheets

(56) References Cited

U.S. PATENT DOCUMENTS

| | | |
|---|---|---|
| 5,733,310 A | 3/1998 | Lopin et al. |
| 5,800,685 A | 9/1998 | Perrault |
| 5,871,505 A | 2/1999 | Adams |
| 5,987,354 A | 11/1999 | Cooper |
| 6,004,312 A | 12/1999 | Finneran et al. |
| 6,006,131 A | 12/1999 | Cooper et al. |
| 6,056,738 A | 5/2000 | Marchitto et al. |
| 6,141,584 A | 10/2000 | Rockwell et al. |
| 6,197,324 B1 | 3/2001 | Crittenden |
| 6,251,100 B1 | 6/2001 | Flock et al. |
| 6,256,533 B1 | 7/2001 | Yuzhakov et al. |
| 6,266,563 B1 | 7/2001 | Kenknight et al. |
| 6,315,722 B1 | 11/2001 | Yaegashi |
| 6,329,488 B1 | 12/2001 | Terry |
| 6,379,324 B1 | 4/2002 | Gartstein et al. |
| 6,477,413 B1 | 11/2002 | Sullivan et al. |
| 6,576,712 B2 | 6/2003 | Feldstein |
| 6,596,401 B1 | 7/2003 | Terry |
| 6,597,948 B1 | 7/2003 | Rockwell et al. |
| 6,611,707 B1 | 8/2003 | Prausnitz |
| 6,690,959 B2 | 2/2004 | Thompson |
| 6,714,817 B2 | 3/2004 | Daynes et al. |
| 6,797,276 B1 | 9/2004 | Glenn |
| 6,803,420 B2 | 10/2004 | Cleary |
| 6,908,453 B2 | 6/2005 | Fleming |
| 6,908,681 B2 | 6/2005 | Terry |
| 6,931,277 B1 | 8/2005 | Yuzhakov |
| 7,072,712 B2 | 7/2006 | Kroll et al. |
| 7,108,681 B2 | 9/2006 | Gartstein |
| 7,215,991 B2 | 5/2007 | Besson et al. |
| 7,226,439 B2 | 6/2007 | Prausnitz |
| 7,463,917 B2 | 12/2008 | Martinez |
| 7,645,263 B2 | 1/2010 | Angel et al. |
| 7,797,044 B2 | 9/2010 | Covey et al. |
| 8,024,037 B2 | 9/2011 | Kumar |
| 8,527,044 B2 | 9/2013 | Edwards et al. |
| 8,558,499 B2 | 10/2013 | Ozaki et al. |
| 8,615,295 B2 | 12/2013 | Savage et al. |
| 8,781,576 B2 | 7/2014 | Savage et al. |
| 9,089,718 B2 | 7/2015 | Owen et al. |
| 9,101,778 B2 | 8/2015 | Savage et al. |
| 9,616,243 B2 | 4/2017 | Raymond et al. |
| 9,656,094 B2 | 5/2017 | Raymond et al. |
| 2001/0031992 A1 | 10/2001 | Fishler et al. |
| 2002/0016562 A1 | 2/2002 | Cormier et al. |
| 2002/0045907 A1 | 4/2002 | Sherman et al. |
| 2002/0082644 A1 | 6/2002 | Picardo et al. |
| 2003/0017743 A1 | 1/2003 | Picardo et al. |
| 2003/0055460 A1 | 3/2003 | Owen et al. |
| 2003/0088279 A1 | 5/2003 | Rissmann et al. |
| 2003/0125771 A1 | 7/2003 | Garrett et al. |
| 2003/0167075 A1 | 9/2003 | Fincke |
| 2003/0197487 A1 | 10/2003 | Tamura et al. |
| 2004/0105834 A1 | 6/2004 | Singh |
| 2004/0143297 A1 | 7/2004 | Ramsey, III |
| 2004/0166147 A1 | 8/2004 | Lundy |
| 2004/0247655 A1 | 12/2004 | Asmus |
| 2005/0055460 A1 | 3/2005 | Johnson et al. |
| 2005/0107713 A1 | 5/2005 | Van Herk |
| 2005/0123565 A1 | 6/2005 | Subramony |
| 2006/0136000 A1 | 6/2006 | Bowers |
| 2006/0142806 A1 | 6/2006 | Katzman et al. |
| 2006/0173493 A1 | 8/2006 | Armstrong et al. |
| 2006/0206152 A1 | 9/2006 | Covey et al. |
| 2007/0016268 A1 | 1/2007 | Carter et al. |
| 2007/0078376 A1 | 4/2007 | Smith |
| 2007/0135729 A1 | 6/2007 | Ollmar et al. |
| 2007/0143297 A1 | 6/2007 | Recio et al. |
| 2007/0150008 A1 | 6/2007 | Jones et al. |
| 2007/0191901 A1 | 8/2007 | Schecter |
| 2008/0082153 A1 | 4/2008 | Gadsby et al. |
| 2008/0097546 A1 | 4/2008 | Powers et al. |
| 2008/0154110 A1 | 6/2008 | Burnes et al. |
| 2008/0154178 A1 | 6/2008 | Carter et al. |
| 2008/0177342 A1 | 7/2008 | Snyder |
| 2008/0312579 A1 | 12/2008 | Chang et al. |
| 2008/0312709 A1 | 12/2008 | Volpe et al. |
| 2009/0005827 A1 | 1/2009 | Weintraub et al. |
| 2009/0076366 A1 | 3/2009 | Palti |
| 2009/0210022 A1 | 8/2009 | Powers |
| 2009/0318988 A1 | 12/2009 | Powers |
| 2009/0326400 A1 | 12/2009 | Huldt |
| 2010/0063559 A1 | 3/2010 | McIntyre et al. |
| 2010/0160712 A1 | 6/2010 | Burnett et al. |
| 2010/0181069 A1 | 7/2010 | Schneider et al. |
| 2010/0191141 A1 | 7/2010 | Aberg |
| 2010/0241181 A1 | 9/2010 | Savage et al. |
| 2010/0249860 A1 | 9/2010 | Shuros et al. |
| 2011/0028859 A1 | 2/2011 | Chian |
| 2011/0071611 A1 | 3/2011 | Khuon et al. |
| 2011/0208029 A1 | 8/2011 | Joucla et al. |
| 2011/0237922 A1 | 9/2011 | Parker, III et al. |
| 2011/0288604 A1 | 11/2011 | Kaib et al. |
| 2011/0301683 A1 | 12/2011 | Axelgaard |
| 2012/0101396 A1 | 4/2012 | Solosko et al. |
| 2012/0112903 A1 | 5/2012 | Kaib et al. |
| 2012/0136233 A1 | 5/2012 | Yamashita |
| 2012/0158075 A1 | 6/2012 | Kaib et al. |
| 2012/0158078 A1 | 6/2012 | Kaib et al. |
| 2012/0203297 A1 | 8/2012 | Efimov et al. |
| 2012/0259382 A1 | 10/2012 | Trier et al. |
| 2013/0018251 A1 | 1/2013 | Caprio et al. |
| 2013/0144365 A1 | 6/2013 | Kipke et al. |
| 2014/0005736 A1 | 1/2014 | Geheb |
| 2014/0039593 A1 | 2/2014 | Savage et al. |
| 2014/0039594 A1 | 2/2014 | Savage et al. |
| 2014/0221766 A1 | 8/2014 | Kinast |
| 2014/0276183 A1 | 9/2014 | Badower |
| 2014/0277226 A1 | 9/2014 | Poore et al. |
| 2014/0317914 A1 | 10/2014 | Shaker |
| 2014/0371566 A1 | 12/2014 | Raymond et al. |
| 2014/0371567 A1 | 12/2014 | Raymond et al. |
| 2014/0371805 A1 | 12/2014 | Raymond et al. |
| 2014/0371806 A1 | 12/2014 | Raymond et al. |
| 2015/0297104 A1 | 10/2015 | Chen et al. |
| 2015/0327781 A1 | 11/2015 | Hernandez-Silveira et al. |
| 2016/0206893 A1 | 7/2016 | Raymond et al. |
| 2016/0213933 A1 | 7/2016 | Raymond et al. |
| 2016/0213938 A1 | 7/2016 | Raymond et al. |
| 2016/0296177 A1 | 10/2016 | Gray et al. |
| 2016/0361533 A1 | 12/2016 | Savage et al. |
| 2016/0361555 A1 | 12/2016 | Savage et al. |
| 2017/0252572 A1 | 9/2017 | Raymond et al. |

FOREIGN PATENT DOCUMENTS

| | | |
|---|---|---|
| EP | 1 834 622 | 9/2007 |
| JP | 2005-144164 | 6/2005 |
| JP | 2007-530124 | 11/2007 |
| JP | 2008-302254 | 12/2008 |
| JP | 2010-511438 | 4/2010 |
| JP | 2010-529897 | 9/2010 |
| JP | 2012-135457 | 7/2012 |
| JP | 2012-529954 | 11/2012 |
| JP | 2000-093526 | 1/2017 |
| JP | 2011-512227 | 9/2017 |
| JP | 2012-501789 | 9/2017 |
| WO | 03/020362 | 3/2003 |
| WO | WO2010/146492 | 12/2010 |
| WO | WO2010/151875 | 12/2010 |

OTHER PUBLICATIONS

PCT Written Opinion of the International Searching Authority of PCT/US10/27346; dated Oct. 14, 2010 (7 pgs.).

PCT International Preliminary Report on Patentability of PCT/US12/65712; dated Jun. 10, 2014 (6 pgs.).

PCT International Search Report of PCT/US14/42355; dated Nov. 3, 2010 (2 pgs.).

PCT Written Opinion of the International Searching Authority of PCT/US14/42355; dated Nov. 3, 2014 (6 pgs.).

PCT International Search Report of PCT/US14/42356; dated Nov. 3, 2010 (2 pgs.).

(56) References Cited

OTHER PUBLICATIONS

PCT Written Opinion of the International Searching Authority of PCT/US14/42356; dated Nov. 3, 2014 (6 pgs.).
PCT International Search Report of PCT/US14/42360; dated Nov. 4, 2010 (2 pgs.).
PCT Written Opinion of the International Searching Authority of PCT/US14/42360; dated Nov. 4, 2014 (4 pgs.).
PCT International Search Report of PCT/US14/42409; dated Nov. 4, 2010 (2 pgs.).
PCT Written Opinion of the International Searching Authority of PCT/US14/42409; dated Nov. 4, 2014 (4 pgs.).
Chinese First Office Action of CN 201080021650.4 (English and Chinese); dated Jul. 24, 2013 (19 pgs.).
Chinese Second Office Action of CN 201080021650.4 (English and Chinese); dated Jan. 16, 2014 (16 pgs.).
Chinese Third Office Action of CN 201080021650.4 (English and Chinese); dated Jun. 17, 2014 (18 pgs.).
Japanese Notification of Reason for Rejection of JP 2012-500855 (English and Japanese); dated Feb. 17, 2014 (3 pgs.).
PCT International Search Report of PCT/US2012/065712, dated Mar. 29, 2013 (2 pages).
PCT Written Opinion of PCT/US2012/065712, dated Mar. 29, 2013 (5 pages).
PCT International Preliminary Report on Patentability and Written Opinion of PCT/EP2007/009879; dated May 19, 2009 (7 pages).
PCT International Search Report of PCT/EP2007/009879; dated Apr. 29, 2008 (3 pages).
PCT International Preliminary Report on Patentability of PCT/US2010/027346 dated Sep. 20, 2011 (12 pages).
Extended European Search Report of EP 2408521 dated Jul. 10, 2012 (8 pages).
"Changes in the passive electrical properties of human stratum corneum due electroporation" dated Dec. 7, 1994. By U. Pliquett, R. Langer, and J. C. Weaver (11 pages).
"Electrical properties of the epidermal stratum corneum" dated Aug. 12, 1974. By T. Yamamoto and Y. Yamamoto (8 pages).
"Non-invasive bioimpedance of intact skin: mathematical modeling and experiments" dated May 2, 2010. By U. Birgersson, E. Birgersson, P. Aberg, I. Nicander, and S. Ollmar (19 pages).
"Polymer Microneedles for Controlled-Release Drug Delivery" dated Dec. 2, 2005. By J-H. Park, M. G. Allen, and M. R. Prausnitz (12 pages).
"Utilizing Characteristic Electrical Properties of the Epidermal Skin Layers to Detect Fake Fingers in Biometric Fingerprint Systems—A Pilot Study" dated Dec. 1, 2004. By O. G. Martinsen, S. Clausen, J. B. Nysaether, and S. Grimnes (4 pages).
"Lack of Pain Associated with Microfabricated Microneedles" dated Oct. 10, 2000. By S. Kaushik, A. H. Hord, D. D. Denson, D. V. McAlliser, S. Smitra, M. G. Allen, and M. R. Prausnitz (3 pages).
"Two Dimensional Metallic Microelectrode Arrays for Extracellular Stimulation and Recording of Neurons" dated 1993. By A. B. Frazier, D. P. O'Brien, and M. G. Allen (6 pages).
"Insertion of microneedles into skin: measurement and prediction of insertion force and needle facture force" dated Dec. 10, 2003. By S. P. Davis, B. J. Landis, Z. H. Adams, M. G. Allen, and M. R. Prausnitz (9 pages).
"Microneedle Insertion Force Reduction Using Vibratory Actuation" dated 2004. By M. Yang and J. D. Zahn (6 pages).
Yamanouchi, et al., *Optimal Small-Capacitor Biphasic Waveform for External Defibrillation; Influence of Phase-1 Tilt and Phase-2 Voltage*, Journal of the American Heart Association, vol. 98, pp. 2487-2493 (8 pgs.).

figure 2 figure 1 figure 4 figure 5 figure 7 figure 8

MULTIPART NON-UNIFORM PATIENT CONTACT INTERFACE AND METHOD OF USE

PRIORITY CLAIMS/RELATED APPLICATIONS

This application claims the benefit under 35 USC 119(e) and 120 to U.S. Provisional Patent Application No. 61/835,465 filed on Jun. 14, 2013 and entitled "Multipart Non-Uniform Sensor Contact Interface and Method of Use" and to U.S. Provisional Patent Application No. 61/835,478 filed on Jun. 14, 2013 and entitled "Multipart Non-Uniform Electrode Contact Interface and Method of Use", the entirety of both of which are incorporated herein by reference.

FIELD

The disclosure relates generally to methods and arrangements relating to medical devices. More specifically, the disclosure relates to systems and methods used in medical device patient contact interfaces especially used in external defibrillators or wearable cardioverter defibrillators.

BACKGROUND

A primary task of the heart is to pump oxygenated, nutrient-rich blood throughout the body. Electrical impulses generated by a portion of the heart regulate the pumping cycle. When the electrical impulses follow a regular and consistent pattern, the heart functions normally and the pumping of blood is optimized. When the electrical impulses of the heart are disrupted (i.e., cardiac arrhythmia), this pattern of electrical impulses becomes chaotic or overly rapid, and a Sudden Cardiac Arrest may take place, which inhibits the circulation of blood. As a result, the brain and other critical organs are deprived of nutrients and oxygen. A person experiencing Sudden Cardiac Arrest may suddenly lose consciousness and die shortly thereafter if left untreated.

The most successful therapy for Sudden Cardiac Arrest is prompt and appropriate defibrillation. A defibrillator uses electrical shocks to restore the proper functioning of the heart. A crucial component of the success or failure of defibrillation, however, is time. Ideally, a victim should be defibrillated immediately upon suffering a Sudden Cardiac Arrest, as the victim's chances of survival dwindle rapidly for every minute without treatment.

There are a wide variety of defibrillators. For example, Implantable Cardioverter-Defibrillators (ICD) involve surgically implanting wire coils and a generator device within a person. ICDs are typically for people at high risk for a cardiac arrhythmia. When a cardiac arrhythmia is detected, a current is automatically passed through the heart of the user with little or no intervention by a third party.

Figure 8:
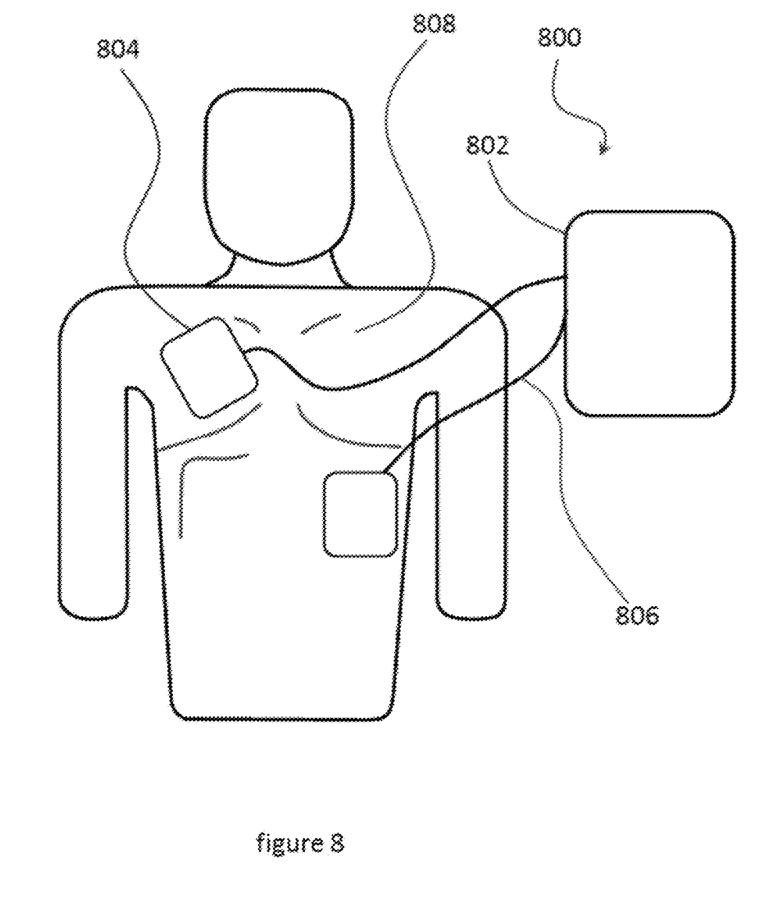
FIG. 8 diagrammatically illustrates an example of a conventional external defibrillator.

Another, more common type of defibrillator is the automated external defibrillator (AED). Rather than being implanted, the AED is an external device used by a third party to resuscitate a person who has suffered from sudden cardiac arrest. FIG. 8 illustrates a conventional AED 800, which includes a base unit 802 and two pads 804. Sometimes paddles with handles are used instead of the pads 804. The pads 804 are connected to the base unit 802 using electrical cables 806.

A typical protocol for using the AED 800 is as follows. Initially, the person who has suffered from sudden cardiac arrest is placed on the floor. Clothing is removed to reveal the person's chest 808. The pads 804 are applied to appropriate locations on the chest 808, as illustrated in FIG. 8. The electrical system within the base unit 800 generates a high voltage between the two pads 804, which delivers an electrical shock to the person. Ideally, the shock restores a normal cardiac rhythm. In some cases, multiple shocks are required.

Although existing technologies work well, there are continuing efforts to improve the effectiveness, safety and usability of automatic external defibrillators.

Accordingly, efforts have been made to improve the availability of automated external defibrillators (AED), so that they are more likely to be in the vicinity of sudden cardiac arrest victims. Advances in medical technology have reduced the cost and size of automated external defibrillators (AED). Some modern AEDs approximate the size of a laptop computer or backpack. Even small devices may typically weigh 4-10 pounds or more. Accordingly, they are increasingly found mounted in public facilities (e.g., airports, schools, gyms, etc.) and, more rarely, residences. Unfortunately, the average success rates for cardiac resuscitation remain abysmally low (less than 1%).

Such solutions, while effective, are still less than ideal for most situations. Assume, for example, that a person suffers from a cardiac arrest in an airport in which multiple AEDs have been distributed. The victim's companion would nevertheless have to locate and run towards the nearest AED, pull the device off the wall, and return to the collapsed victim to render assistance. During that time, precious minutes may have passed. According to some estimates, the chance of surviving a sudden cardiac arrest is 90% if the victim is defibrillated within one minute, but declines by 10% for every minute thereafter. A defibrillator design that reduces the time to defibrillation by even two to three minutes will save more lives.

An additional challenge is that a sudden cardiac arrest may take place anywhere. People often spend time away from public facilities and their homes. For example, a sudden cardiac arrest could strike someone while biking in the hills, skiing on the mountains, strolling along the beach, or jogging on a dirt trail. Ideally, an improved AED design would be compact, light, and resistant to the elements and easily attached or detached from one's body. The typical AED design illustrated in FIG. 8, which includes a sizable console or power unit whose form factor is similar to that of a laptop or backpack, seems less than ideal for the outdoors and other rigorous environments.

New and improved designs are allowing AEDs to become ultra-portable and hence to able to be easily carried by an at-risk person as they go about all of their daily activities and thus are able to be close at hand when a sudden cardiac arrest strikes outside of a hospital environment or a high traffic public area with a Public Access Defibrillator.

There are also improvements being made in the area of device usability and ease of operation for untrained bystanders. As noted above, every minute of delay or distraction can substantially decrease the victim's probability of survival. As a result, it is generally beneficial to streamline the operation of the external defibrillator so that a user of the defibrillator, who is presumably under substantial mental duress, can focus his or her attention on a few key variables.

Another type of defibrillator is the Wearable Cardioverter Defibrillator (WCD). Rather than a device being implanted into a person at-risk from Sudden Cardiac Arrest, or being used by a bystander once a person has already collapsed from experiencing a Sudden Cardiac Arrest, the WCD is an external device worn by an at-risk person which continuously monitors their heart rhythm to identify the occurrence of an arrhythmia, to then correctly identify the type of arrhythmia involved and then to automatically apply the therapeutic action required for the type of arrhythmia identified, whether this be cardioversion or defibrillation. These devices are most frequently used for patients who have been identified as potentially requiring an ICD and to effectively protect them during the two to six month medical evaluation period before a final decision is made and they are officially cleared for, or denied, an ICD.

External Defibrillators and Automated External Defibrillators on the market today make use of either rigid paddles that must be held in place on the patient's body or else flexible electrode pads (made of conductive foil and foam) which are stuck to the patient's skin. The current external defibrillators that have rigid paddle bases do not conform to the curvatures of the patient's body at the locations on the body where the paddles must be placed in order to be effective. As such the operators of these devices must apply a good amount of contact force to make physical contact across the paddle's patient contact interface and must maintain this force to maximize the surface area in contact with the patient for the sensing and reading of the heart rhythm in order that the device can detect the presence of a faulty rhythm, or arrhythmia, such as Ventricular Fibrillation or Ventricular Tachycardia so as to instruct/initiate or signal the external defibrillator to deliver the life saving therapeutic defibrillation shock pulse. The operator must also continue holding the required contact force while the device delivers the chosen therapeutic action (shock or no shock).

There are medical, practical and commercial needs to make new AEDs which are smaller, potentially even flexible, and hence much more discrete in order for patients to be able to carry the devices around with them as they go about their daily lives. This means that the life saving device is always with them for a bystander to use immediately if they drop from a Sudden Cardiac Arrest. This is far preferable to the current system of having a few AEDs mounted on the walls of a limited number of the most high traffic public locations.

Wearable Cardioverter Defibrillators on the market today are still bulky and uncomfortable for the patients to wear. They utilize a single source of energy in a box that attaches to the wearable garment (containing the sensors and the electrodes) and the energy source box normally rides on the hip. These are heavy and uncomfortable to wear and a frequent source of complaints from patients.

Current Wearable Cardioverter Defibrillators have fixed flat surface electrodes and fixed curved surface electrodes for positioning on the patient's back and abdomen. This requires that each patient has to be specially fitted for their own unit, which is time consuming for the patient. Given the limited range of device sizes available it also requires that the device be worn tightly in order to maintain a constant contact pressure with both the sensors and the electrodes, which is restrictive and can be uncomfortable for the patient. This is also the reason why the devices also employ the use of liquid conductive hydrogel, to ensure that the electrode-to-patient contact impedance is minimized. This is messy to clean up after each use when deployed by the device, and naturally this can adversely impact the patient's clothing. It also requires that the liquid reservoirs be recharged before the device can be effectively used again.

There are medical, practical and commercial needs to make new WCDs smaller and more flexible, more comfortable and more discrete for patients to wear as they go about their daily lives.

DETAILED DESCRIPTION OF ONE OR MORE EMBODIMENTS

The disclosure is particularly applicable to a pliable patient contact interface that may be used with a wearable AED and it is in this context that the disclosure will be described. It will be appreciated, however, that the patient contact interface has greater utility since it may be used with any medical device or other system in which it is desirable to be able to conform a patient contact interface to a non-flat surface.

A way to improve AEDs and wearable AEDs is to make it so that the circuitry and the energy source/reservoir may be re-distributed from the one large container/enclosure found in existing AEDs into two or more smaller containers. Each of these smaller containers has their own circuitry and energy source/reservoir and they are also combined with the ECG sensors and a defibrillation shock electrode. The two smaller containers are then connected to each other electrically and packaged together for easy transportation. In the wearable AED system, the two or more smaller containers may be mounted on the body of the patient. The smaller and more effective that the sensors and the electrodes can be made the better, which means ensuring that they maximize the surface area in contact with the patient's skin and also maximize the quality of the contact with the patient's skin. The system thus allows AEDs and WCDs to be made smaller, potentially flexible, more comfortable and much more discrete.

The patient contact interface disclosed assists with an optimal contact being maintained with the patient and hence that the device-to-patient impedance is minimized without requiring that the patient be either fastened into a garment as tight fitting as a corset before being able to reliably sense a continuous ECG, or be dowsed in liquid conductive hydrogel before being administered a therapeutic shock.

The patient contact interface may employ a mix of sensor types, such as ECG sensors and LED optical pulse detectors, rather than the traditional use of just ECG sensors. This mix means that the AED's or WCD's accuracy of the detection of shockable arrhythmias can be significantly improved and hence the incidence of unnecessary shocks can be significantly reduced and hence in addition the need for a patient to use any shock override button is reduced. The mix of sensor types may further include sensors which can be active in nature, passive in nature, or a combination of the two types. A passive sensor may be a sensor, like an ECG sensor, that just passively picks up a reading or signal, without taking any action itself. An active sensor may be a sensor, like a Pulse Oximeter, that actively performs a function such as shining a light into the patient's flesh in order to detect and analyze the reflected light from the blood flow in the patient's nearby blood vessels and hence identify the levels of oxygenation of that blood.

One embodiment of the patient contact interface allows external defibrillators with rigid paddles to provide a greater contact surface area with the patient's body, and an improved consistency of physical contact between the patient contacts and the patient's skin through using the natural tendency of the skin to give and conform to the shape of an object pressing into it without the need for the operator to apply excessive contact force. The use of the multi-part non-uniform patient contact interface ensures that there are multiple different contact points, each of which take advantage of the skin's natural tendency to give and conform, which ensures that a single contact location attaining a poor level of contact does not prevent the collection of the needed sensor readings nor the delivery of necessary therapy.

The patient contact interface can also be embodied to work with a wearable AED, or a Wearable Cardioverter Defibrillator, and this can be mounted on the patient in a number of different ways and in a number of different locations. The invention provides a more consistent contact surface area with the patient's body through the use of the multi-part non-uniform patient contact interface approach.

Through the utilization of a pliable yet stable substrate into which the multi-part non-uniform patient contact interface is embedded the invention can be flexed, wrapped and secured around almost any contours found at the relevant locations on a patient's body whilst maintaining a gentle pressure which ensures that a high quality level of device-to-patient contact is maintained. This improved consistency of physical contact between the patient contacts and the patient's skin is aided by the natural tendency of the skin to give and conform to the shape of any object pressing into it without the need for the operator to apply excessive contact force.

Figure 1:
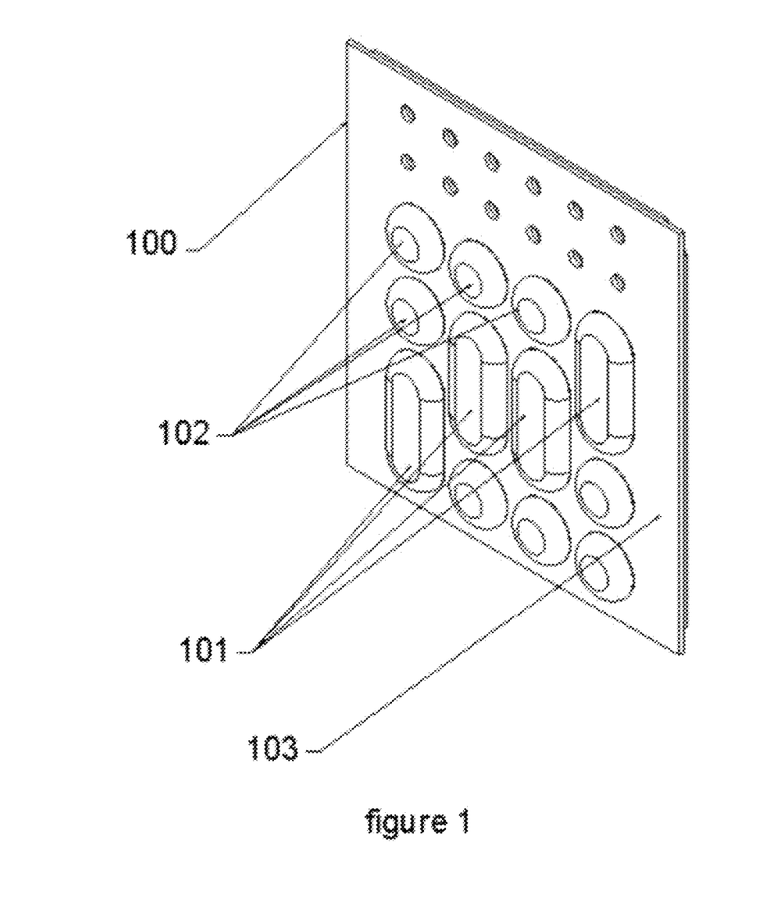
FIG. 1 illustrates the external patient-facing side of the patient contact assembly exhibiting several potential patient contact element shapes.
Figure 2:
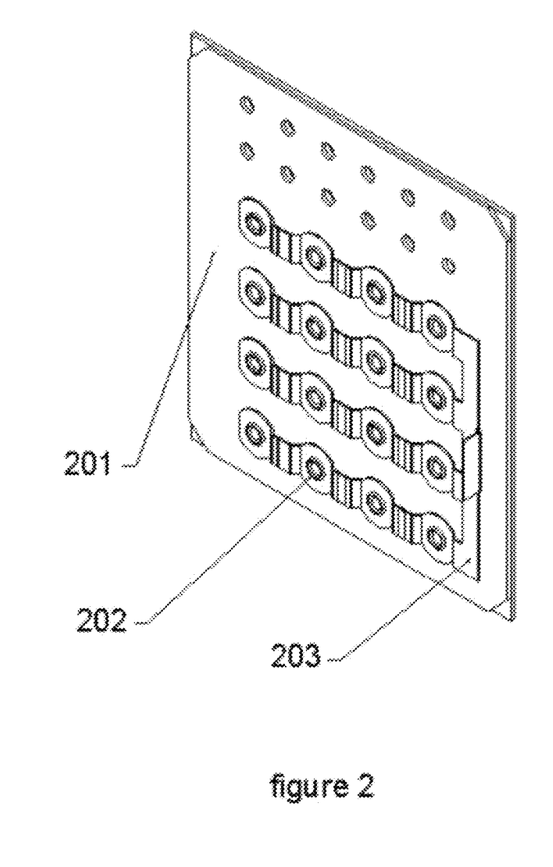
FIG. 2 illustrates the reverse side of FIG. 1 exhibiting the internal electrical contacts and patient contact element anchor locations.
Figure 6:
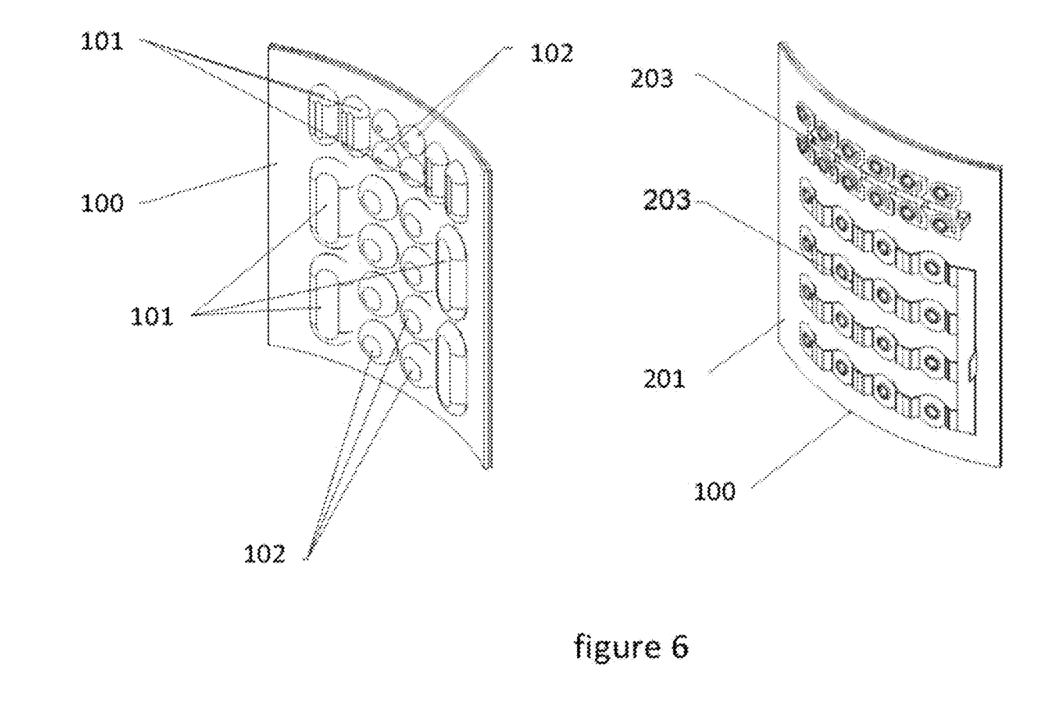
FIG. 6 illustrates a flexible patient contact assembly.

FIGS. 1 and 6 illustrate an external patient-facing side of the patient contact assembly (100) exhibiting several potential patient contact element shapes and FIG. 2 illustrates the reverse side of FIG. 1 exhibiting the internal electrical contacts and patient contact element anchor locations. The patient facing side of the patient contact assembly (100) may be made up of a set of patient contact elements shown here in the shapes of one or more "Bars" (101) and one or more "Buttons" (102). The contact elements may vary in shape, size and number to suit the precise embodiment need of the equipment with which they are being used, and provide the best results. The patient contact elements 101, 102 may be one or more sensors, one or more electrodes or a combination of one or more sensors and one or more electrodes. In some implementations in which the patent interface assembly has both sensors and electrodes, the sensors and electrodes may each be located separately from each other. In other implementations in which the patent interface assembly has both sensors and electrodes, the sensors and electrodes may be intermixed with each other in the patient interface assembly.

The arrangement of the patient contact elements may be varied and may include a single contact element, an array of contact elements, a portion of the assembly with bar contact elements and a portion of the assembly with button contact elements as shown in FIG. 1 and the like. In other embodiments, the patient contact elements, the bars (101) and buttons (102), may be simultaneously and contiguously formed along with and as part of the contact substrates (201).

The patient interface assembly described in this document may be placed onto a body of a patient and may be used, for example, to sense the heartbeat of the patient and then deliver a therapeutic pulse to the patient for defibrillation for example. The patient interface assembly may also be used to deliver other types of treatments of varying during to the patient. The patient interface assembly may also be used to sense a characteristic of the patient, such as a heartbeat or pulse and the like. The patient interface assembly may also be used to both sense a characteristic of the patient and deliver a treatment to the patient when the patient interface assembly has both sensors and electrodes.

The patient contact assembly may be placed onto the body of the patient at various locations, such as the torso, limbs and/or head of the patient. In some implementations, multiple patient contact assemblies may be used and each patient contact assembly may be placed on one or more locations on the body of the patient. In some embodiments, the patient contact assembly may have one or more patient contacts 101, 102 as shown in FIG. 1 and each patient contact may have the same particular shape (which is not shown in FIG. 1.) In other implementations, the patient contact assembly may have one or more patient contacts 101, 102 as shown in FIG. 1 and each patient contact may have a variety of shapes such as those shown in FIG. 1 for example. Similarly, each patient contact may be similarly sized or differently sized as shown in FIG. 1.

The assembly (100) may have a substrate (103) to which the contact elements are attached. In one embodiment, a material of the substrate (103) in between the bars (101) and buttons (102) may be conductive (where the patient contact elements are conductive) and another embodiment where this material is not conductive (where the patient contact elements are conductive.) In another embodiment, the material of the substrate (103) may be constructed of the same material used for the bars (101) and buttons (102) and is formed from the same single piece of this material. In a different embodiment, the substrate (103) may be constructed of the same material but it is yet formed from separate pieces of this material.

While the patient contact elements may be constructed from conductive material, such as stainless steel, the range of embodiments allow for the inclusion of multiple types of sensor elements such as optical sensors, electrical sensors, temperature sensors or even complex micro circuits or micro-mechanical circuits which may be used to fulfill a variety of functions and which may not be constructed from a conductive material. In the multi-part non-uniform patient contact interface assembly (100) a single type of sensor, or electrode, or multiple different types of sensors, or electrodes, can be incorporated individually, or in separated groups, and partially or fully intermixed within the same multi-part non-uniform patient contact interface assembly (100). The sensor elements, along with a similarly wide variety of potential electrode elements, can be implemented individually or as part of one large extended array, or as multiple smaller arrays, or in any combination of these approaches.

FIGS. 2 and 6 show the back side (the non-patient facing side) of the multi-part non-uniform patient contact interface assembly (100). In one embodiment of the patient contact elements, the bars (101) and buttons (102), are separately formed and are attached to a contact substrates (201). The contact elements are installed and, using a swage process, the ends of the contact elements (305) are rolled over forming a solid physical and electrical contact (202) to an interconnecting circuit assembly (203) that electrically connects the patient contact elements to each other. The interconnecting circuit assembly (203) also allows the patient contact elements to be electrically connected to a power source to be able to, for example, deliver a therapeutic pulse to a patient. An end of the patient contact element before the swage process is a cylindrical shape and a finished shape (303) shows the ends of the patient contact elements post swage process.

Figure 3:
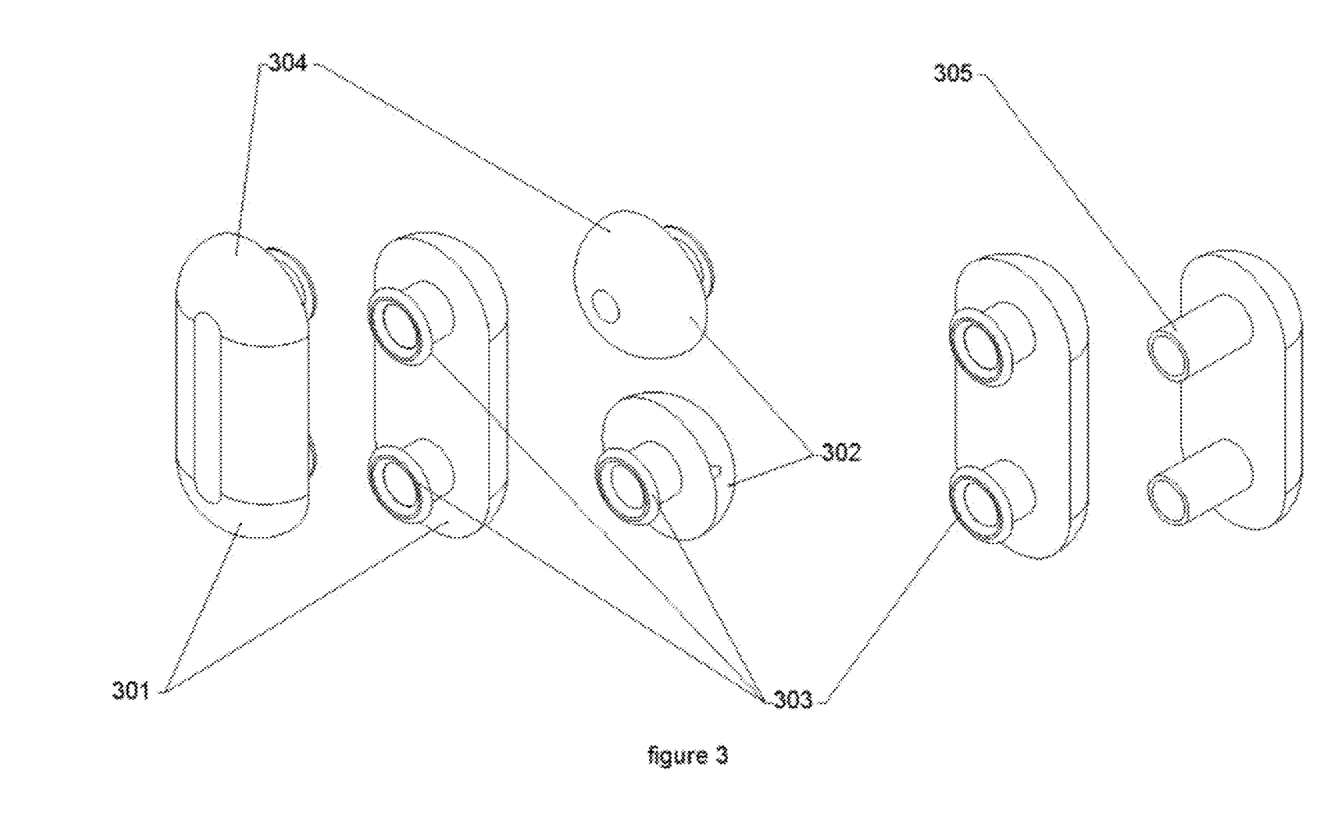
FIG. 3 illustrates various shaped patient contact elements before and after being swaged.
Figure 4:
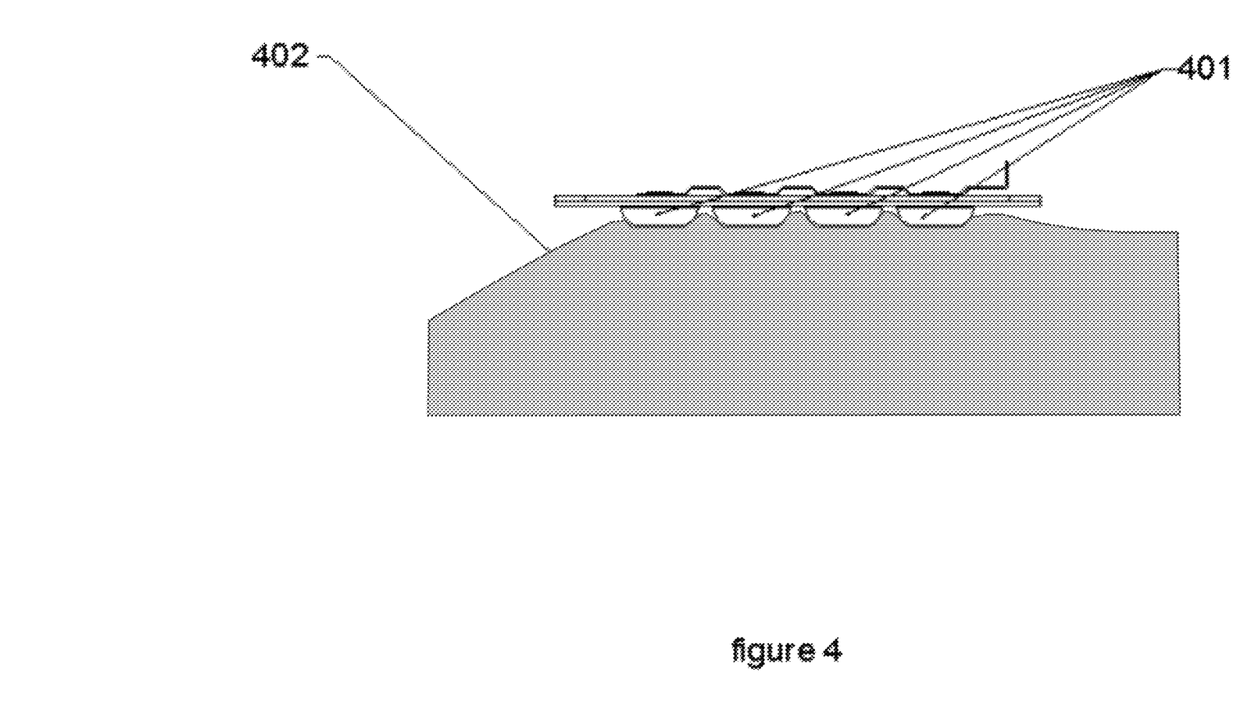
FIG. 4 illustrates the contact between a patient's skin and the patient contact assembly.

FIG. 3 shows the details of the Bar contacts (301) and Button contacts (302). The front surface (304) in contact with the patient of the Bar contact (301) and Button contact (302) has a gentle curved smooth surface, providing comfort to the Patient skin. This smooth surface allows the pliable dermis/epidermis to give and conform to the shape of the Bar contacts (301) and Button contacts (302), as shown in FIG. 4. The contact Bars and Buttons (401) are shown in contact with the Patient's skin (402) in FIG. 4. The pliable nature of the patient's dermis/epidermis ensures that the skin deforms and fills in the gaps between the Bars and Buttons contact elements and effectively increases the total contact area.

Figure 5:
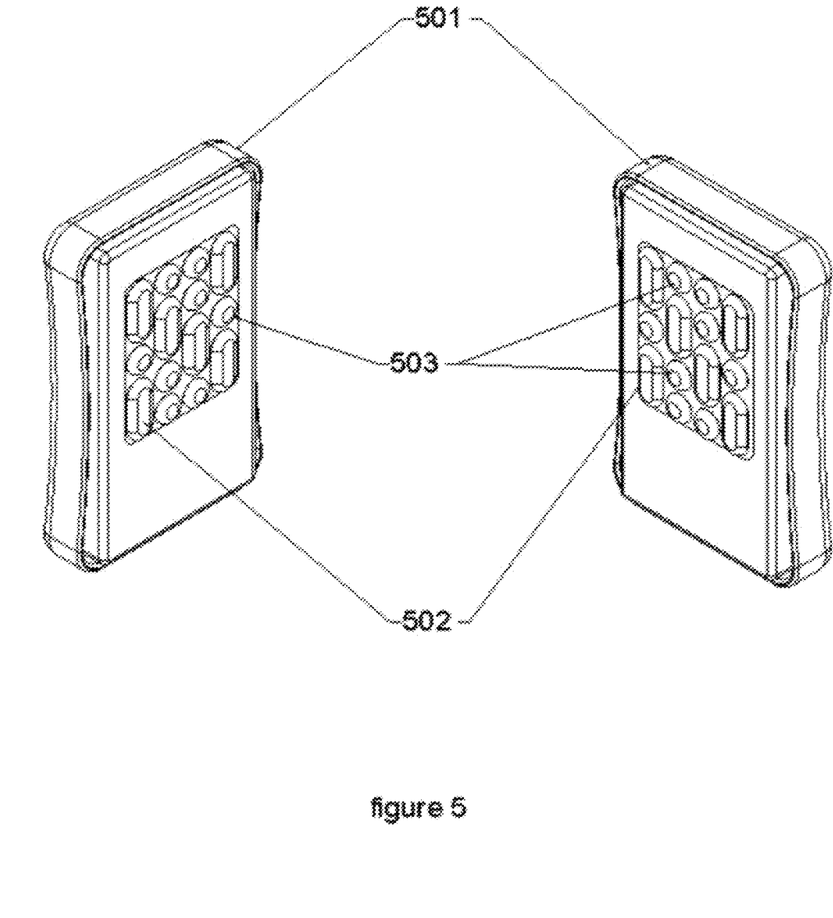
FIG. 5 illustrates a medical device incorporating a patient contact assembly within a rigid patient-facing surface.

FIG. 5 illustrates a medical device incorporating a patient contact assembly within a rigid patient-facing surface of a defibrillator paddle, or other medical device. The multi-part non-uniform patient contact (502 and 503) may be located on the rigid paddle (501). The contact structure may be a mix of Bar contact elements (502) and Button contact elements (503) which are arranged as required for optimal contact with the Patient's skin.

FIG. 6 illustrates a flexible patient contact assembly. As shown, if the substrate (201) is pliable and flexible, then the patient contact assembly may be flexible and bend (as shown in FIG. 6) to fit around various differently shaped anatomical structures of the patient.

Figure 7:
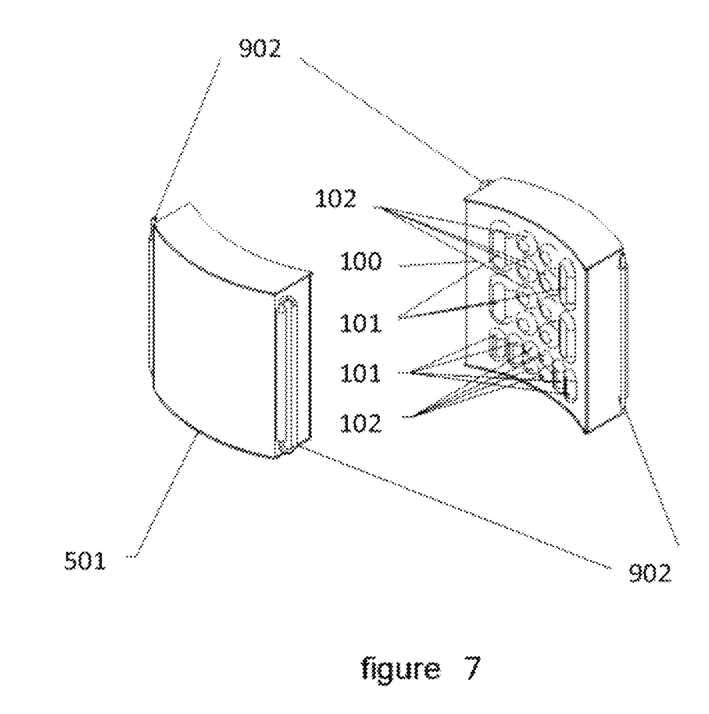
FIG. 7 illustrates a medical device incorporating a patient contact assembly within a pliable/flexible patient-facing surface.

FIG. 7 illustrates a medical device incorporating a patient contact assembly within a pliable/flexible patient-facing surface. In this example, the multi-part non-uniform patient contact interface assembly (100) is anchored to a pliable/flexible body (501) of a wearable defibrillator interface, or other wearable medical device. The multi-part non-uniform patient contacts (101 and 102) may be connected to the flexible body or wearable interface (501). The contact structure may be a mix of Bar contact elements (101) and Button contact elements (102) which are arranged as required for optimal contact with the Patient's skin.

The described Multi-part Non-uniform Patient Contact Interface allows for ideal Patient body contact without the need for the device operator to directly apply sustained contact force. An adhesive on the edge of the Defibrillator paddle may hold the assembly in place while the flexibility of the Multi-part Non-uniform Patient Contact Interface contacts the Patient body. The patient contact assembly may reduce the need for the operator to be in contact with the Defibrillator or Patient, removing the risk to the operator and reducing the risk to the patient.

The patient contact interface may allow for the weight of the rigid device that it is part of to be reduced or the flexibility of the pliable substrates that it is built with to be maintained along with its method of attachment to the patient. The patient contact interface sustains the high quality contact between the patient contact elements and the patient's skin, despite the movements of the operator or of the patient.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A patient interface assembly, comprising:
   a substrate;
   a plurality of three-dimensionally contoured electrically conductive patient contacts physically attached to a first side of the substrate, each of the plurality of patient contacts having a top surface and a curved side portion surface that is connected to the top surface and holds the top surface above the first side of the substrate;
   an interconnecting circuit assembly on a side of the substrate opposite from the first side of the substrate that electrically connects the plurality of three-dimensionally contoured patient contacts; and
   wherein the top surface and curved side portion surface of the plurality of patient contacts provide contact with an uneven contact surface when the patient interface assembly is placed against the uneven contact surface.

2. The assembly of claim 1, wherein each patient contact has a particular shape.

3. The assembly of claim 1, wherein each of the plurality of patient contacts has a same shape.

4. The assembly of claim 1, wherein the plurality of patient contacts have one or more different sizes.

5. The assembly of claim 4, wherein the differently sized contacts are connected to the substrate.

6. The assembly of claim 1, wherein each patient contact is a sensor.

7. The assembly of claim 6, wherein the sensor is one of an ECG sensor and a pulse oximeter.

8. The assembly of claim 1, wherein the plurality of patient contacts are selected from an ECG sensor and a pulse oximeter.

9. The assembly of claim 1, wherein each patient contact is an electrode.

10. The assembly of claim 1, wherein the plurality of patient contacts are one or more sensors and one or more electrodes.

11. The assembly of claim 10, wherein the one or more sensors are arranged in the configuration separately from the one or more electrodes.

12. The assembly of claim 10, wherein the one or more sensors are arranged in the configuration intermixed with the one or more electrodes.

13. The assembly of claim 1, wherein the plurality of patient contacts are spaced and make the patient interface assembly capable of flexing and conforming to the contours of the uneven surface when the patient interface assembly is placed on the uneven surface.

14. The assembly of claim 1, wherein the plurality of patient contacts further comprises one or more bar patient contacts and one or more button patient contacts.

15. The assembly of claim 1 wherein each of the patient contacts has a flat top surface and a curved portion extending from the top surface down to the first side of the substrate.

16. The assembly of claim 1, wherein the plurality of three-dimensionally contoured electrically conductive patient contacts further comprises a particular three-dimensionally contoured electrically conductive patient contact attached to the first side of the substrate with a space between the particular three-dimensionally contoured electrically conductive patient contact and an adjacent three-dimensionally contoured electrically conductive patient contact.

\* \* \* \* \*